(12) United States Patent
Klee

(10) Patent No.: US 10,278,901 B2
(45) Date of Patent: May 7, 2019

(54) DENTAL COMPOSITION

(71) Applicant: DENTSPLY SIRONA Inc., York, PA (US)

(72) Inventor: Joachim Klee, Radolfzell (DE)

(73) Assignee: DENTSPLY SIRONA INC, York, PA (US)

( * ) Notice: Subject to any disclaimer, the term of this patent is extended or adjusted under 35 U.S.C. 154(b) by 0 days.

(21) Appl. No.: 15/323,161

(22) PCT Filed: Jul. 2, 2015

(86) PCT No.: PCT/EP2015/065062
§ 371 (c)(1),
(2) Date: Dec. 30, 2016

(87) PCT Pub. No.: WO2016/001344
PCT Pub. Date: Jan. 7, 2016

(65) Prior Publication Data
US 2017/0156992 A1 Jun. 8, 2017

(30) Foreign Application Priority Data

Jul. 2, 2014 (EP) ..................................... 14175414

(51) Int. Cl.
| | |
|---|---|
| *A61K 6/087* | (2006.01) |
| *C07D 301/16* | (2006.01) |
| *C07D 303/23* | (2006.01) |
| *C08L 63/00* | (2006.01) |
| *A61K 6/00* | (2006.01) |
| *C08G 59/06* | (2006.01) |
| *C08G 59/24* | (2006.01) |
| *C08G 59/32* | (2006.01) |
| *C08G 59/50* | (2006.01) |

(52) U.S. Cl.
CPC ............ *A61K 6/087* (2013.01); *A61K 6/0038* (2013.01); *A61K 6/0047* (2013.01); *A61K 6/0073* (2013.01); *C07D 301/16* (2013.01); *C07D 303/23* (2013.01); *C08G 59/063* (2013.01); *C08G 59/245* (2013.01); *C08G 59/3218* (2013.01); *C08G 59/50* (2013.01); *C08L 63/00* (2013.01)

(58) Field of Classification Search
CPC ...................................................... A61K 6/087
See application file for complete search history.

(56) References Cited

U.S. PATENT DOCUMENTS

| | | | | |
|---|---|---|---|---|
| 5,236,362 A | * | 8/1993 | Cohen ................... | A61K 6/002 433/224 |
| 5,624,976 A | * | 4/1997 | Klee ..................... | A61K 6/0038 433/228.1 |
| 8,044,113 B2 | | 10/2011 | Klee | |
| 2008/0234404 A1 | * | 9/2008 | Klee .................... | A61K 6/0038 523/116 |

FOREIGN PATENT DOCUMENTS

| | | |
|---|---|---|
| WO | 2013120610 A2 | 8/2013 |
| WO | 2014025406 A1 | 2/2014 |

OTHER PUBLICATIONS

Written Opinion of the International Searching Authority dated Jul. 14, 2015.

\* cited by examiner

*Primary Examiner* — Michael F Pepitone
(74) *Attorney, Agent, or Firm* — Dentsply Sirona Inc.

(57) ABSTRACT

Dental composition comprising
(a) at least two di- or polyepoxides having 2 to 5 epoxide groups and having a molecular weight of from 200 to 700 Da, or a macromonomeric reaction product obtainable by reacting the diepoxide with a dicarboxylic acid in a molar ratio [diepoxide]/[dicarboxylic acid] of at least 2;
(b) one or more primary monoamines and/or disecondary diamines;
(c) optionally one or more aliphatic polyamines;
(d) a particulate filler,
wherein the molar ratio of epoxide groups in component (a) to the N—H bonds in component (b) and (c) [epoxide$_{(a)}$]/[N—H$_{(b),(c)}$] is in the range of from 0.9 to 1.1;
wherein the di- or polyepoxide having 2 to 5 epoxide groups is a compound of the following formula (I):

$$A(BZ_m)_n \qquad (I)$$

wherein
A represents an n-valent organic moiety optionally having 1 to 10 heteroatoms selected from oxygen atoms and sulfur atoms; and
B represents an m+1-valent organic moiety,
Z is an epoxide group which may have a substituent,
m which are independent from each other represent an integer of at least 1; and
n is an integer of from 1 to 5;
wherein the m are selected so that 2 to 5 epoxide groups are present;
wherein the composition does not contain any 2,2-bis-(4-hydroxyphenyl)-propane, or 2,2-bis-(4-hydroxyphenyl)-methane.

10 Claims, No Drawings

DENTAL COMPOSITION

CROSS-REFERENCE TO RELATED APPLICATIONS

This patent application is national stage of International application PCT/EP2015/065062, filed Jul. 2, 2015 and claims the benefit of and priority to EP Application Ser. No. 14175414.3, filed on Jul. 2, 2014, which is herein incorporated by reference for all purposes.

FIELD OF THE INVENTION

The present invention relates to a dental composition which does not contain any bisphenol-A or bisphenol-F, or preferably even an estrogen mimicking derivative thereof. Moreover, the present invention relates to a process for preparing a composition according to the present invention. Finally, the present invention relates to a di- or polyepoxide having 2 to 5 epoxide groups obtainable by the process according to the present invention.

The dental composition according to the present invention is particularly useful as a root canal sealing composition or a pulp capping composition. According to the present invention, a specific di- or polyepoxide component is used in an epoxide/amine polymerization system. The specific di- or polyepoxide contained in the dental composition according to the present invention may be used for avoiding bisphenol-A or bisphenol-F based components such as bisphenol-A diglycidyl ether or bisphenol-F diglycidyl ether in a root canal sealing composition or pulp capping composition due to favourable mechanical properties of the cured compositions and the low viscosity of the uncured compositions, as well as the small dimensional changes of the compositions upon curing. Advantageously, the specific di- or polyepoxide contained in the dental composition according to the present invention may also provide short gel times.

BACKGROUND OF THE INVENTION

Dental compositions for endodontic purposes are desired to approach natural tooth structure with regard to physical properties and biocompatibility. Moreover, good handling properties are also desired. Accordingly, a great effort is documented by the prior art directed to the development of dental compositions for endodontic purposes, which have improved properties with regard to physical properties, biocompatibility, and handling properties.

In the case of a dental root canal sealing composition, the main objective is to achieve a high degree of tightness of the root canal filling. The quality of the root canal filling directly depends on the shrinkage upon setting and the solubility of the material used, as these properties are decisive for the impermeability of the treated root canal.

Moreover, a low viscosity of the composition is required in order to allow penetration of the composition into the dentin of the root canal and in order to facilitate the complete filling of the root canal including any cavities which could not be accessed by a high viscosity composition with insufficient flow properties. Moreover, in order to maintain a tight seal, the dental root canal sealing composition should have good adhesion to hard dental structure including dentin.

Dental compositions selected from a root canal sealing composition and a pulp capping composition are subject to additional requirements in that the cured product is required to have a high radioopacity. The contrast of the material in the root canal as observed by x-ray diagnostic methods permits conclusions regarding the quality of the filling. Accordingly, a particulate filler having high radioopacity is incorporated into the composition. Suitable filler materials have a high density and are prone to settle out from the dental composition during storage which gives rise to a stability problem of the composition which is aggravated when the viscosity of the composition is low. Therefore, a dilemma exists between to the viscosity of the composition and the storage stability of the composition. Furthermore, the storage stability may also be limited in case of precipitation of solid components dissolved or dispersed in the dental composition.

Moreover, dental compositions selected from a root canal sealing composition and a pulp capping composition that the composition are required to be curable in the absence of light. In order to be able to cure a root canal sealing composition or pulp capping composition in the absence of light, the composition is cured by a thermal curing mechanism which may involve step growth polymerizing epoxide precursor compounds such as bisphenol-A diglycidylether or bisphenol-F diglycidylether with amine precursors. Bisphenol-A diglycidyl ether or bisphenol-F diglycidylether provide an excellent combination of properties for the purpose of a dental compositions including a favourable gel time in step-growth polymerizations with a diamine or polyamine. Moreover, favourable mechanical properties of the cured compositions while the viscosity of the uncured compositions may be adjusted to be comparably low, and a low shrinkage of the compositions upon curing are reasons for the widespread use of bisphenol-A or bisphenol-F diglycidylether based materials in the dental field.

From the prior art, a dental root canal sealer is known which consists of a paste-paste system AH Plus®. A first paste contains a diepoxide, calcium tungstate, zirconium oxide, aerosil, and a pigment. A second paste contains 1-adamantane amine, N,N'-dibenzyl-5-oxa-nonandiamine-1,9, TCD-diamine, calcium tungstate, zirconium oxide, aerosil, silicone oil. The composition cures in a step growth polyaddition reaction into a thermoplastic material. The polyaddition reaction of AH Plus® requires several hours whereby the gel time is about 16 hours.

Bisphenol-A and also bisphenol-F are known endocrine disrupters which can mimic estrogen and may lead to negative health effects. In particular, bisphenol A mimics the structure and function of the hormone estradiol with the ability to bind to and activate the same estrogen receptor as the natural hormone. Based on the functional relevance of bisphenol-A it is considered that bisphenol-A might contribute to the development of breast cancer. Accordingly, regulatory bodies might determine safety levels of bisphenol-A for humans so that the use of bisphenol-A based materials containing bisphenol A in a dental composition cannot be continued in the future.

At present, any of the commercially available root canal sealers based on epoxide-amine chemistry contain bisphenol-A diglycidylether (DGEBA): AH Plus® (DENTSPLY), AH 26 (DENTSPLY), Asphaline® (Alfred Becht GmbH), Acroseal® (Septodont), Adseal® (META BIOMED), Perma Evolution® (META BIOMED), EZ-Fill® (Essential Dental Systems).

WO 2013/120610 discloses a curable filler material mixture, comprising an epoxy as component (a), an amine as component (b), and a quaternary ammonium salt as component (c). The mixture contains a single epoxy as component (a), which may be resorcinol diglycidyl ether.

SUMMARY OF THE INVENTION

Accordingly, it is the problem of the present invention to provide a dental composition including a root canal sealing composition and a pulp capping composition, having properties including physical properties of the cured composition, dispersion stability and handling properties of the uncured composition, and biocompatibility, which are at least on the level of corresponding bisphenol-A or bisphenol-F based materials, while the composition does not contain any 2,2-bis-(4-hydroxyphenyl)-propane, 2,2-bis-(4-hydroxyphenyl)-methane. Preferably, the dental compositions do not contain even an estrogen mimicking derivative of 2,2-bis-(4-hydroxyphenyl)-propane, or 2,2-bis-(4-hydroxyphenyl)-methane. Moreover, the compositions should have a reduced gel time and provide adhesion to the dentin of a dental root canal in order to further improve the tight sealing of a root canal.

It is a further problem of the present invention to provide a process for preparing the dental composition including a root canal sealing composition and a pulp capping composition, which is economic and technically realisable and which may be carried out on a scale which is industrially relevant for the preparation of a dental composition.

Finally, it is the problem of the present invention to provide a polymerizable compound obtainable in the process of the present invention as well as a use of the polymerizable compound for the preparation of a dental composition.

According to a first aspect, the present invention provides a dental composition comprising
(a) at least two di- or polyepoxides having 2 to 5 epoxide groups and having a molecular weight of from 200 to 700 Da, or a macromonomeric reaction product obtainable by reacting the diepoxide with a dicarboxylic acid in a molar ratio [diepoxide]/[dicarboxylic acid] of at least 2;
(b) one or more primary monoamines and/or disecondary diamines;
(c) one or more aliphatic polyamines;
(d) a particulate filler,
wherein the molar ratio of epoxide groups in component (a) to the N—H bonds in component (b) and (c) [epoxide(a)]/[N—H(b),(c)] is in the range of from 0.9 to 1.1; wherein the di- or polyepoxide having 2 to 5 epoxide groups is a compound of the following formula (I):

$A(BZ_m)_n$ (I)

wherein
A represents an n-valent organic moiety optionally having 1 to 10 heteroatoms selected from oxygen atoms and sulfur atoms; and
B represents an m+1-valent organic moiety,
Z is an epoxide group,
m which are independent from each other represent an integer of at least 1; and
n is an integer of from 1 to 5;
wherein the m are selected so that 2 to 5 epoxide groups are present;
wherein the composition does not contain any 2,2-bis-(4-hydroxyphenyl)-propane, 2,2-bis-(4-hydroxyphenyl)-methane, and preferably does not contain derivatives thereof.

According to a second aspect, the present invention provides a process for preparing a composition according to the first aspect, which comprises reacting one or more compounds having 2 to 5 hydroxyl groups with epichlorohydrine for preparing a di- or polyepoxide having 2 to 5 epoxide groups as defined by the first aspect.

According to a third aspect, the present invention provides a di- or polyepoxide having 2 to 5 epoxide groups obtainable by the process according to any one of the second aspect.

A dental composition according to the present invention may be provided as a root canal sealing composition and a pulp capping composition having properties including physical properties of the cured composition, dispersion stability and handling properties of the uncured composition, and biocompatibility, which are at least on the level of corresponding bisphenol-A or bisphenol-F based materials, while the composition does not contain any 2,2-bis-(4-hydroxyphenyl)-propane, 2,2-bis-(4-hydroxyphenyl)-methane or preferably even an estrogen mimicking derivative thereof.

DETAILED DESCRIPTION OF THE PREFERRED EMBODIMENTS

The term "radioopacity" refers to a substance that will not allow X-rays or similar radiation to pass and or thereby allows X-ray visibility.

The term "derivative of 2,2-bis-(4-hydroxyphenyl)-propane, 2,2-bis-(4-hydroxyphenyl)-methane" relates to compounds having the ability to bind to and activate the same estrogen receptor as the natural hormone. Examples of the derivatives are bisphenol AF (CAS: 1478-61-1), bisphenol B (CAS: 77-40-7), bisphenol C (CAS: 79-97-0), alpha,alpha-bis(4-hydroxyphenyl)trichloroethane (CAS: 2971-36-0), bisphenol E (CAS: 2081-08-5), bisphenol F (CAS: 620-92-8), bisphenol M (CAS 13595-25-), bisphenol S (CAS 80-09-1), bisphenol Z (CAS843-55-0), 4,4-(hexahydro-4,7-methanoindan-5-ylidene)diphenol (CAS: 1943-97-1), 4,4-hydroxybenzophenone (CAS: 611-99-4), 2,2-bis(4-hydroxyphenyl)propionic acid (CAS 92549-67-2), 2,2-bis(4-hydroxyphenyl)propanol (CAS: 142648-65-5), 4,4'-MBTBT (CAS: 118-82-1), and 4,4'-thiobisphenol (CAS: 2664-63-3). In general, derivatives are diols or polyols wherein two phenolic hydroxyl groups are capable of mimicking the interactions of the same estrogen receptor as estradiol of the following formula:

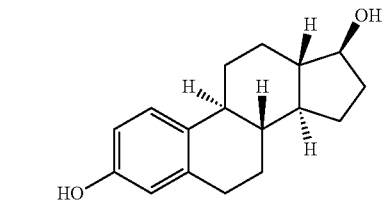

Estradiol is characterized by a distance between the hydroxyl groups of about 10.1 Angstrom. Bisphenol A is characterized by a distance between the hydroxyl groups of 9.0 Angstroms. Preferably, a derivative avoids an arrangement of two hydroxyl groups which facilitates the ability of the derivative to bind to and activate the same estrogen receptor as the natural hormone.

The present invention provides a dental composition. Preferably, the dental composition is a dental root canal sealing composition or a dental pulp capping composition. The composition of the present invention does not contain any 2,2-bis-(4-hydroxyphenyl)-propane or 2,2-bis-(4-hydroxyphenyl)-methane, or preferably even an estrogen mimicking derivative thereof. Accordingly, the starting materials of the composition of the present invention are not prepared by using any 2,2-bis-(4-hydroxyphenyl)-propane, or 2,2-bis-(4-hydroxyphenyl)-methane or preferably even an estrogen mimicking derivative thereof so that the composition of the present invention may contain unreacted 2,2-bis-(4-hydroxyphenyl)-propane, 2,2-bis-(4-hydroxyphenyl)-methane or derivatives thereof, or so that the composition of the present invention may leach out 2,2-bis-(4-hydroxyphenyl)-propane, 2,2-bis-(4-hydroxyphenyl)-methane or derivatives thereof due to hydrolytic cleavage of bonds which anchor 2,2-bis-(4-hydroxyphenyl)-propane, 2,2-bis-(4-hydroxyphenyl)-methane or derivatives thereof in the cured composition.

The dental composition of the present invention comprises (a) at least two di- or polyepoxides having 2 to 5 epoxide groups. The di- or polyepoxides have a molecular weight of from 200 to 700 Da. Preferably, the molecular weight is in the range of 250 to 600 Da.

Alternatively, component (a) may be a macromonomeric reaction product obtainable by reacting the diepoxide of the formula (I) with a dicarboxylic acid in a molar ratio [diepoxide]/[dicarboxylic acid] of at least 2. The macromonomeric reaction product is an epoxide capped molecule which may take part in the epoxide/amine curing reaction with components (b) and/or (c). The dicarboxylic acid may be selected from terephthalic acid, isophthalic acid, 2,6-naphthalene dicarboxylic acid, diphenyl-4,4-dicarboxylic acid, oxalic acid, malonic acid, succinic acid, glutaric acid, adipic acid, pimelic acid, suberic acid, azelaic acid, sebacic acid, undecanedioic acid, and/or dodecanedioic acid. The reaction may be carried out according to Otera; Matsuzaki, Synthesis 1986, 1019; or Deardorff; Myles Org. Synth. 67, 114, which provides beta-hydroxyalkyl carboxylates by the treatment of the diepoxide with a dicarboxylic acid or the corresponding carboxylate ions in the presence of a suitable catalyst.

The di- or polyepoxide having 2 to 5 epoxide groups is a compound of the following formula (I):

$$A(BZ_m)_n \quad (I)$$

In formula (I), A represents an n-valent organic moiety optionally having 1 to 10 heteroatoms selected from oxygen atoms and sulfur atoms. The term "organic moiety" in relation to residue A means a moiety which may be based in general on a hydrocarbon group having 1 to 50 carbon atoms, preferably 2 to 30 carbon atoms, including aliphatic, alicyclic, or aromatic moieties or a combination thereof. Preferably, the organic moiety consists of, or contains an aromatic moiety. The organic moiety links or connects further moieties. Accordingly, the organic moiety has a valency which corresponds to the number of further moieties. In a compound of formula (I), a $A(BZ_m)_n$, the group A represents an n-valent organic moiety optionally having 1 to 10 heteroatoms selected from oxygen atoms and sulfur atoms. The heteroatoms may form part of a carbon chain of the hydrocarbon group, and/or the heteroatoms may form a functional group such as a carboxyl group, a hydroxyl group, a thiol group, or a keto group. According to a preferred embodiment, wherein the heteroatoms selected from oxygen atoms and sulfur atoms in groups A are present in ester bonds, ether bonds, thioester bonds or thioether bonds. According to a preferred embodiment, A contains an aromatic ring. Preferably, A is a 1,3-phenylene derivative.

Examples of aliphatic moieties include alkyl groups. According to the invention, a $C_{1-20}$ alkyl group can include straight or branched alkyl groups having 1 to 20 carbon atoms, preferably 1 to 10 carbon atoms, for example, methyl, ethyl, n-propyl, isopropyl, n-butyl, isobutyl, sec-butyl, tert-butyl, n-pentyl, isopentyl and n-hexyl. Examples of a group A which is an n-valent aliphatic moiety optionally having 1 to 10 heteroatoms selected from oxygen atoms and sulfur atoms, are alkylene groups, polyoxyalkylene groups such as polyoxyethylene groups or polyoxypropylene groups. When n is 2, then an aliphatic moiety is preferably a $C_{2-12}$ alkylene group, more preferably a $C_{2-8}$ alkylene group.

The alicyclic moieties may include, for example, a $C_{3-6}$ carbocyclic aliphatic ring, a $C_{3-6}$ heterocyclic aliphatic ring, a $C_{3-6}$ saturated aliphatic ring, or a $C_{3-6}$ unsaturated aliphatic ring. Examples of alicyclic groups include cycloalkyl or cycloalkylalkyl groups. A cycloalkyl group may be a $C_{3-6}$ cycloalkyl group. Examples of the cycloalkyl group can include those having 3 to 6 carbon atoms, for example, cyclopropyl, cyclobutyl, cyclopentyl and cyclohexyl. A cycloalkylalkyl group can include those having 4 to 8 carbon atoms. Examples for a cycloalkylalkyl group can include a combination of a straight or branched alkyl group having 1 to 6 carbon atoms and a cycloalkyl group having 3 to 6 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, and propylcyclopentyl. Examples of a group A which is an n-valent alicyclic moiety optionally having 1 to 10 heteroatoms selected from oxygen atoms and sulfur atoms, are polyoxyalkylene groups such as polyoxyethylene groups or polyoxypropylene groups.

An aromatic moieties may include a phenyl group or a naphtyl group. Preferred moieties of A include the following structures (i) and (ii):

(i)

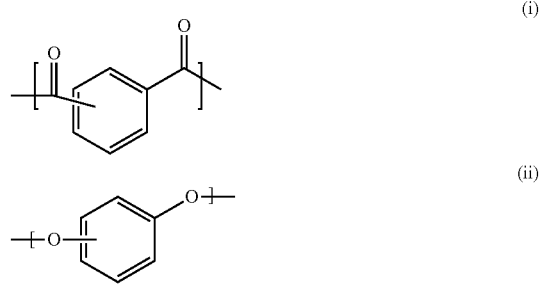

(ii)

In view of shortening the gel time of the dental composition of the present invention, it is preferred that A is (ii).

It has been found that with identical di- or polyamine components, aromatic glycidyl ethers, e.g. of formula (ii) provide a reduced gelling time as compared to the corresponding aromatic glycidyl esters, e. g. according to (i).

Specific examples of groups A containing one or more aromatic rings may be derived from bisphenol AP (CAS: 1571-75-1), bisphenol BP (CAS: 1844-01-5), bisphenol FL (CAS: 3236-71-3), bisphenol G (CAS: 127-54-8), bisphenol P (CAS: 2167-51-3), bisphenol PH (CAS: 24038-68-4), bisphenol TMC (CAS: 129188-99-4), alpha,alpha bi-para-phenol (CAS: 6052-84-2), or resorcinol.

In Formula (I), B represents an m+1-valent organic moiety. The term "organic moiety" in relation to residue B relates to a moiety which may be based in general on a hydrocarbon group having 1 to 30 carbon atoms, preferably 1 to 20 carbon atoms, including aliphatic, alicyclic, or aromatic moieties or a combination thereof. The organic moiety is linked to a group A. When the group B is linked to an aromatic group A, then the connecting functional group may be a phenolic ether group, a benzylic ether group or an ester group. In view of an increase of the gel time, it is preferable that the connecting functional group is a phenolic ether group or a benzylic ether group. According to a more preferred embodiment, the connecting functional group is a phenolic ether group.

The organic moiety links or connects further moieties. Accordingly, the organic moiety has a valency which corresponds to the number of further moieties. In a compound of formula (I), a $A(BZ_m)_n$, the group B represents an m+1-valent organic moiety optionally having 1 to 10 heteroatoms selected from oxygen atoms and sulfur atoms. The heteroatoms may form part of a carbon chain of the hydrocarbon group, and/or the heteroatoms may form a functional group such as a carboxyl group, a hydroxyl group, a thiol group, a keto group, an ester group or a thioester group.

Examples of aliphatic moieties include alkyl groups. According to the invention, a $C_{1-20}$ alkyl group can include straight or branched alkyl groups having 1 to 20 carbon atoms, preferably 1 to 10 carbon atoms, for example, methyl, ethyl, n-propyl, isopropyl, n-butyl, isobutyl, sec-butyl, tert-butyl, n-pentyl, isopentyl and n-hexyl. Examples of a group A which is an n-valent aliphatic moiety optionally having 1 to 10 heteroatoms selected from oxygen atoms and sulfur atoms, are polyoxyalkylene groups such as polyoxyethylene groups or polyoxypropylene groups.

The alicyclic moieties may include, for example, a $C_{3-6}$ carbocyclic aliphatic ring, a $C_{3-6}$ heterocyclic aliphatic ring, a $C_{3-6}$ saturated aliphatic ring, or a $C_{3-6}$ unsaturated aliphatic ring. Examples of alicyclic groups include cycloalkyl or cycloalkylalkyl groups. A cycloalkyl group may be a $C_{3-6}$ cycloalkyl group. Examples of the cycloalkyl group can include those having 3 to 6 carbon atoms, for example, cyclopropyl, cyclobutyl, cyclopentyl and cyclohexyl. A cycloalkylalkyl group can include those having 4 to 8 carbon atoms. Examples for a cycloalkylalkyl group can include a combination of a straight or branched alkyl group having 1 to 6 carbon atoms and a cycloalkyl group having 3 to 6 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, and propylcyclopentyl. Examples of a group A which is an n-valent alicyclic moiety optionally having 1 to 10 heteroatoms selected from oxygen atoms and sulfur atoms, are polyoxyalkylene groups such as polyoxyethylene groups or polyoxypropylene groups An aromatic moieties may include a phenyl group or a naphtyl group.

Z is an epoxide group which may have a substituent. The substituent may be selected from a straight chain or branched $C_{1-6}$ alkyl group. Preferably, Z is an unsubstituted epoxide group.

In a group $BZ_m$, a single moiety B carries at least one epoxide group Z. In case a moiety B carries more than one epoxide group Z, the structure of the epoxide groups Z, i.e. the presence or absence and the nature of the substituent of the epoxide group are independent from each other. The epoxide group Z may form part of the main chain of moiety B. Alternatively, the epoxide group Z may be present as an end group of the main chain or a side chain of moiety B. Preferably, a group B does not contain more than 4 epoxide groups, more preferably a group B contains 1 or 2 epoxide groups. Accordingly, m is preferably an integer of from 1 to 5, more preferably 1 to 4, still more preferably 1 or 2.

In formula (I), n is an integer of from 1 to 5. Accordingly, in a compound of formula (I), at least one $BZ_m$ group is present. Moreover, in a compound of formula (I), at most five $BZ_m$ group are present. If more than one $BZ_m$ group is present, then the $BZ_m$ groups may be the same or different.

The $BZ_m$ groups are selected so that 2 to 5 epoxide groups are present. Preferably, a compound of formula (I) has two or three epoxide groups. According to a preferred embodiment, BZ is a group of the formula (II) or (III):

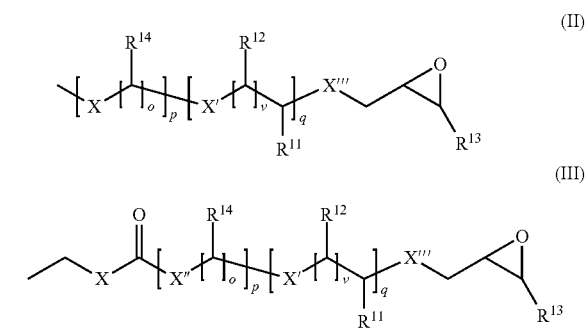

wherein
X is —NH—, an oxygen atom or a sulfur atom,
X' is —NH—, an oxygen atom or a sulfur atom,
X'' is —NH—, an oxygen atom or a sulfur atom,
X''' is —$CH_2$—, —NH—, an oxygen atom or a sulfur atom,
$R^{11}$ and $R^{12}$ which may be the same or different, independently represent a hydrogen atom or a straight chain or branched $C_{1-6}$ alkyl group,
$R^{13}$ represents a hydrogen atom or a straight chain or branched $C_{1-6}$ alkyl group,
$R^{14}$ represents a hydrogen atom, a hydroxyl group which may be substituted, or a straight chain or branched $C_{1-6}$ alkyl group,
o represents an integer of from 2 to 10,
p is an integer of from 0, 1 or 2;
q which may be the same or different, independently represent an integer of from 0 to 10; v represents an integer of from 1 to 10.

In a group of the formula (II) or (III), p and/or q may be 0. Accordingly, if p is 0, then the group of the formula (II) or (III) does not contain an optionally substituted oxyalkylene or polyoxyalkylene spacer moiety. Moreover, if q is 0, then the group of the formula (II) or (III) does not contain an optionally substituted alkylene spacer moiety.

A compound of formula (I) is preferably obtainable by reacting a compound having 2 to 5 hydroxyl groups with epichlorohydrine (1-chloro-2,3-epoxypropane). Preferably, the compound having 2 to 5 hydroxyl groups contains phenolic hydroxyl groups.

A compound of formula (I) may be prepared by reacting a compound having 2 to 5 hydroxyl groups with epichlorohydrine. The epoxidation reaction of the polyol with epichlorohydrin is known from H. Lee and K. Neville, Handbook of Epoxy Resin, Chap. 2, McGraw-Hill, New York (1967), and P. A. Oyanguren and R. J. J. Williams, Polymer, 33, 2376 (1992) and is believed to occur in two steps: in the first step an intermediate chlorohydrin is formed. In a second step, dehydrohalogenation occurs whereby a glycidyl ether is formed.

The following specific compounds of formula (I) may be given:

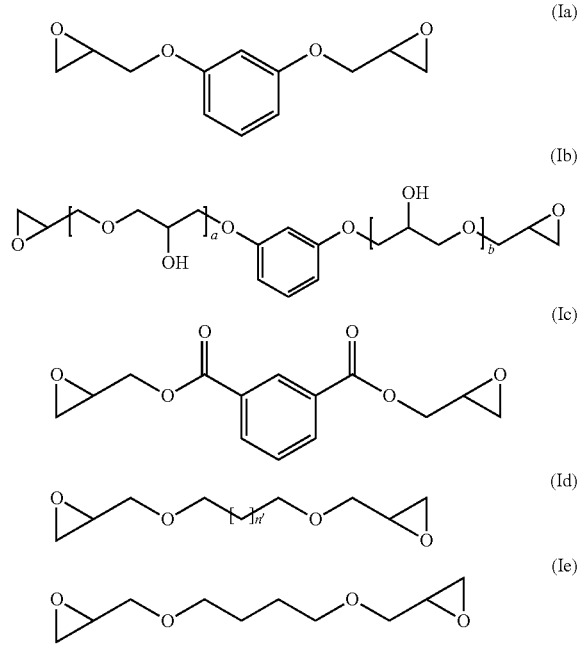

wherein a and b are integers of at least 1 and n' is 0 or an integer of at least 1.

According to a specific embodiment, a combination of an aromatic and a non-aromatic compound of formula (I) is used. Specifically, the aromatic compound of formula (I) may be compound (Ia), (Ib), and/or (Ic). The non-aromatic compound of formula (I) may be compound (Id), in particular compound (Ie).

The dental composition according to the present invention preferably comprises two or more di- or polyepoxides having 2 to 5 epoxide groups in order to prevent precipitation of a di- or polyepoxides from the dental composition. The two or more di- or polyepoxides may be used in about equimolar amounts in the composition. Alternatively, the two or more di- or polyepoxides may be used in amounts so that the amounts of epoxide groups belonging to each compound are present in about equimolar amounts, which differs from equimolar amounts of the di- or polyepoxides in case of different numbers of epoxide groups per molecule. In general, it is preferred that each of the two or more di- or polyepoxides is present in an amount of at least 5 percent by weight, more preferably at least 10 percent by weight based on the total weight of the di- or polyepoxides.

The dental composition according to the present invention further contains (b) one or more primary monoamines and/or disecondary diamines. Component (b) is reactive with the epoxides of component (a) in an epoxide/amine reaction. A primary monoamines may be a compound of the following formula (IV):

$$R-NH_2 \quad (IV)$$

wherein R is a monovalent aliphatic moiety which may be substituted by an aromatic group. However, aromatic amines are not preferred. The term "aliphatic moiety" in relation to residue R relates to a moiety which may be based in general on an aliphatic hydrocarbon group having 1 to 30 carbon atoms, preferably 1 to 20 carbon atoms, which may contain a straight chain, branched chain, or non-aromatic ring or a combination thereof, and which is preferably a saturated moiety. The group R may optionally contain 1 to 10 heteroatoms selected from oxygen atoms and sulfur atoms. The heteroatoms may form part of a carbon chain, and/or the heteroatoms may form a functional group such as a hydroxyl group, a thiol group, a keto group, an ester group or a thioester group.

Examples of aliphatic moieties include alkyl groups. A $C_{1-20}$ alkyl group can include straight or branched alkyl groups having 1 to 20 carbon atoms, preferably 1 to 10 carbon atoms, for example, methyl, ethyl, n-propyl, isopropyl, n-butyl, isobutyl, sec-butyl, tert-butyl, n-pentyl, isopentyl and n-hexyl. Examples of a group R which is an n-valent aliphatic moiety optionally having 1 to 10 heteroatoms selected from oxygen atoms and sulfur atoms, are polyoxyalkylene groups such as polyoxyethylene groups or polyoxypropylene groups.

The alicyclic moieties may include, for example, a $C_{3-20}$ carbocyclic aliphatic ring, a $C_{3-20}$ heterocyclic aliphatic ring, a $C_{3-20}$ saturated aliphatic ring, or a $C_{3-20}$ unsaturated aliphatic ring. Examples of alicyclic groups include cycloalkyl or cycloalkylalkyl groups. A cycloalkyl group may be a $C_{3-6}$ cycloalkyl group. Examples of the cycloalkyl group can include those having 3 to 6 carbon atoms, for example, cyclopropyl, cyclobutyl, cyclopentyl and cyclohexyl. A cycloalkylalkyl group can include those having 4 to 8 carbon atoms. Examples for a cycloalkylalkyl group can include a combination of a straight or branched alkyl group having 1 to 6 carbon atoms and a cycloalkyl group having 3 to 6 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, and propylcyclopentyl. R may also be a polycylic group such as an adamantyl group.

The monovalent aliphatic moiety may be substituted by an aromatic group such as a phenyl group or a naphthyl group.

Examples of a primary monoamine may be selected from benzylamine, 2-phenylethylamine, cyclohexylamine, decylamine and dodecylamine.

An disecondary diamine may be a compound of the following formula (V):

$$R'NHR''NHR''' \quad (V)$$

In formula (V), R' and R'' represent a monovalent aliphatic moiety which may be substituted by an aromatic group. R' and R''' may be the same or different. The term "aliphatic moiety" in relation to residues R' and R''' relates to a moiety which may be based in general on an aliphatic hydrocarbon group having 1 to 30 carbon atoms, preferably 1 to 20 carbon atoms, which may contain a straight chain, branched chain, or non-aromatic ring or a combination thereof, and which is preferably a saturated moiety. The group R' and R''' may optionally contain 1 to 10 heteroatoms selected from oxygen atoms and sulfur atoms. The heteroatoms may form part of a carbon chain, and/or the heteroatoms may form a functional group such as a hydroxyl group, a thiol group, a keto group, an ester group or a thioester group.

Examples of aliphatic moieties include alkyl groups. A $C_{1-20}$ alkyl group can include straight or branched alkyl groups having 1 to 20 carbon atoms, preferably 1 to 10 carbon atoms, for example, methyl, ethyl, n-propyl, isopropyl, n-butyl, isobutyl, sec-butyl, tert-butyl, n-pentyl, isopentyl and n-hexyl.

The alicyclic moieties may include, for example, a $C_{3-20}$ carbocyclic aliphatic ring, a $C_{3-20}$ heterocyclic aliphatic ring, a $C_{3-20}$ saturated aliphatic ring, or a $C_{3-20}$ unsaturated aliphatic ring. Examples of alicyclic groups include cycloalkyl or cycloalkylalkyl groups. A cycloalkyl group may be a $C_{3-6}$ cycloalkyl group. Examples of the cycloalkyl group can include those having 3 to 6 carbon atoms, for example, cyclopropyl, cyclobutyl, cyclopentyl and cyclohexyl. A cycloalkylalkyl group can include those having 4 to 8 carbon atoms. Examples for a cycloalkylalkyl group can include a combination of a straight or branched alkyl group having 1 to 6 carbon atoms and a cycloalkyl group having 3 to 6 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, and propylcyclopentyl. R' and R''' may also be a polycylic group such as an adamantyl group.

In formula (V), R'' is a divalent aliphatic moiety. The term "aliphatic moiety" in relation to residue R'' relates to a moiety which may be based in general on an aliphatic hydrocarbon group having 1 to 30 carbon atoms, preferably 2 to 20 carbon atoms, which may contain a straight chain, branched chain, or non-aromatic ring or a combination thereof, and which is preferably a saturated moiety. The group R'' may optionally contain 1 to 10 heteroatoms selected from oxygen atoms and sulfur atoms. The heteroatoms may form part of a carbon chain, and/or the heteroatoms may form a functional group such as a hydroxyl group, a thiol group, a keto group, an ester group or a thioester group.

Examples of aliphatic moieties of R'' include alkylene groups. A $C_{1-20}$ alkylene group can include straight or branched alkylene groups having 1 to 20 carbon atoms, preferably 1 to 10 carbon atoms, for example, methylene, ethylene, n-propylene, isopropylene, n-butylene, isobutylene, sec-butylene, tert-butylene, n-pentylene, isopentylene and n-hexylene. Examples of a group R'' which is an n-valent aliphatic moiety optionally having 1 to 10 heteroatoms selected from oxygen atoms and sulfur atoms, are polyoxyalkylene groups such as polyoxyethylene groups or polyoxypropylene groups.

The alicyclic moieties may include, for example, a $C_{3-20}$ carbocyclic aliphatic ring, a $C_{3-20}$ heterocyclic aliphatic ring, a $C_{3-20}$ saturated aliphatic ring, or a $C_{3-20}$ unsaturated aliphatic ring. Examples of alicyclic groups include cycloalkylene or cycloalkylalkylene groups. A cycloalkylene group may be a $C_{3-6}$ cycloalkylene group. Examples of the cycloalkylene group can include those having 3 to 6 carbon atoms, for example, cyclopropylene, cyclobutylene, cyclopentylene and cyclohexylene. A cycloalkylalkylene group can include those having 4 to 8 carbon atoms. Examples for a cycloalkylalkylene group can include a combination of a straight or branched alkylene group having 1 to 6 carbon atoms and a cycloalkyl group having 3 to 6 carbon atoms.

Examples of the disecondary diamine of the formula (V) may be selected from N,N'-dibenzyl-5-oxanonane diamine-1,9, N,N'-dibenzylethylenediamine, N,N'-dibenzyltrimethylenediamine, N,N'-dibenzylhexamethylenediamine, N,N'-dimethylhexamethylenediamine, N,N'-diethyl-2,2,4-trimethylhexamethylene diamine, N,N'-di(cyclohexyl)-2,4,4-trimethylhexamethylenediamine and N,N'-di(cyclohexyl) hexamethylenediamine.

The dental composition according to the present invention may optionally further contain (c) one or more aliphatic polyamines. The aliphatic polyamines may contain functional groups such as ether groups, ester groups, or hydroxyl groups. Preferably, an aliphatic polyamine is selected among compounds of the following structures:

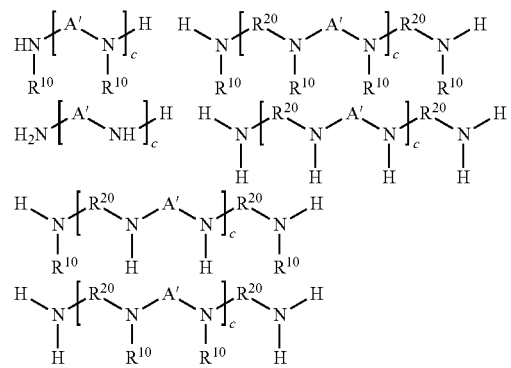

wherein
$R^{10}$ denotes hydrogen or a substituted or unsubstituted $C_1$ to $C_{18}$ alkyl group, a substituted or unsubstituted $C_3$ to $C_{18}$ cycloalkyl group, or a substituted or unsubstituted $C_7$ to $C_{18}$ aralkyl group,
$R^{20}$ represents a difunctional substituted or unsubstituted $C_1$ to $C_{18}$ alkylene group, or a substituted or unsubstituted cycloalkylene group,
A' denotes a moiety derived from a compound that is capable of an addition reaction with amines such as di- or polyepoxides,
c is an integer.

The substituent of the groups of $R^{10}$ and $R^{20}$ may be selected from $C_1$ to $C_{18}$ alkyl groups such as a methyl group, an ethyl group, a propyl group, a butyl group, a pentyl group or a hexyl group. The alkyl groups may be straight chain or branched alkyl groups.

Specific examples of the aliphatic polyamines are selected from Jeffamin T403, Jeffamin T3000, and Jeffamin T5000.

Component (c) may be used for improving the curing properties of the dental composition, including the gel time. Accordingly, if present, component (c) is incorporated preferably in an amount of from 5 to 95 percent by weight based on the total amount of (b) and (c) in the dental composition of the present invention. According to a preferred embodiment, the gel time of the dental composition of the present invention is at most 15 hours, more preferably at most 4 hours and still more preferably at most 1 hours.

The dental composition according to the present invention comprises (d) a particulate filler. Preferably, the dental composition of the invention contains 40 to 85 wt.-% of a filler for providing a minimum radioopacity of the cured composition of at least 3 mm/mm Al. The filler may contain $La_2O_3$, $ZrO_2$, $BiPO_4$, $CaWO_4$, $BaWO_4$, $SrF_2$, $Bi_2O_3$. The radioopacity of the cured composition of the invention is at least 3 mm Al, preferably at least 5 to 7 mm Al, and most preferably at least 7 mm Al.

In the dental composition of the present invention, the molar ratio of epoxide groups in component (a) to the N—H bonds in component (b) and (c) [epoxide(a)]/[N—H(b),(c)] is in the range of from 0.9 to 1.1. Preferably, the molar ratio is about 1.

Preferably, the dental root canal sealing composition of the invention does not contain a diluent, in particular a reactive diluent. Moreover, the dental composition does not need to contain a polymerisation initiator. In a preferred embodiment, the dental root canal sealing composition consists essentially of components (a), (b) and (d), or (a) to (d). A dental root canal sealing composition consisting essentially of components (a), (b) and (d), or (a) to (d) may contain common additives used in the dental field such as colorants, antibiotic agents and ion releasing agents, in a total amount of not more than 25 wt.-%, preferably not more than 10 wt. % of the composition.

The dental root canal sealing composition of the present invention is preferably a two component composition which is mixed prior to use. The two component composition is preferably a powder/liquid system, a powder/paste system, a paste/paste system or a liquid/paste system. The paste/paste system or a liquid/paste system may be applied by an applicator wherein both components are mixed by a static mixer.

The dental composition of the present invention preferably has a viscosity at 23° C. of less than 100 Pa*s. Preferably, the viscosity of the prepolymer is in the range of from 1 to 80 Pa*s, more preferably from 1 to 20 Pa*s. If the viscosity is too high, then it will be difficult to apply the composition through the canal of a needle. If the viscosity is too low, then it will be difficult handle the composition.

The dental root canal sealing composition of the present invention is curable in the absence of a polymerisation initiator. The curing mechanism is based on an addition reaction between component (a) and components (b)/(c).

A composition of the present invention may be applied to a root canal by using conventional techniques. Specifically, the compositions of the present invention may be applied via the needle of a syringe into the root canal.

Moreover, the compositions of the present invention may also be used for the manufacture of prefabricated root canal cones. If cones made of the compositions of the invention are used in combination with the respective dental root canal sealing composition of the invention, compatibility of the cones with the sealing composition can be guaranteed whereby a tight seal may be obtained. The cured product obtained with the composition according to the invention has superior mechanical properties, in particular with regard to flexibility, which is essential for the application as a root canal sealing composition.

EXAMPLES

Reference Example 1—AG 19-24-1

A dental root canal sealing material is obtained by mixing homogeneously 20.000 g (89.993 mmol) recorcinol diglycidyl ether, 9.644 g (89.993 mmol) benzylamine and 70.000 g CaWO$_4$. This dental material has a gelation time of 1.5 hours (at 37° C.) and a radiopacity of 9.4 mm Al.

Reference Example 2—AG 19-24-2

A dental root canal sealing material is obtained by mixing homogeneously 5.239 g (23.574 mmol) recorcinol diglycidyl ether, 8.027 g (23.574 mmol) N,N'-dibenzyl-5-oxanonane diamine-1,9 and 35.780 g ZrO$_2$. This dental material has a gelation time of 8 hours (at 37° C.) and a radiopacity of 10.1 mm Al.

Reference Example 3—AG 19-24-3

A dental root canal sealing material is obtained by mixing homogeneously 12.230 g (55.031 mmol) recorcinol diglycidyl ether, 13.227 g (55.031 mmol) N,N'-dibenzylethylene-diamine and 35.780 g CaWO$_4$. This dental material has a gelation time of 6 hours (at 37° C.) and a radiopacity of 6.1 mm/mm Al.

Reference Example 4—AG 19-24-4

A dental root canal sealing material is obtained by mixing homogeneously 9.300 g (33.422 mmol) phthalic acid diglycidylester, 11.381 g (33.422 mmol) N,N'-dibenzyl-5-oxanonane diamine-1,9 and 62.300 g CaWO$_4$. This dental material has a gelation time of 20 hours (at 37° C.) and a radiopacity of 10.4 mm Al.

Example 5—AG

A dental root canal sealing material is obtained by mixing homogeneously 2.000 g (8.999 mmol) recorcinol diglycidyl ether, 0.182 g (0.900 mmol) butanediol diglycidylether, 3.371 g (9.899 mmol) N,N'-dibenzyl-5-oxanonane diamine-1,9 and 32.000 g CaWO$_4$. This dental material has a setting time of 13 hours (at 37° C.) and a radiopacity of 16.0±0.4 mm/mm Al.

Example 6—AG

A dental root canal sealing material is obtained by mixing homogeneously 2.000 g (8.999 mmol) recorcinol diglycidyl ether, 1.820 g (8.999 mmol) butanediol diglycidylether, 6.129 g (17.999 mmol) N,N'-dibenzyl-5-oxanonane diamine-1,9 and 65.000 g CaWO$_4$. This dental material has a setting time of 19 hours (at 37° C.) and a radiopacity of 15.9±0.1 mm/mm Al.

All of the commercially available root canal sealers basing on epoxide-amine chemistry contain Bisphenol-A diglycidylether (DGEBA): AH Plus (DENTSPLY), AH 26 (DENTSPLY), Asphaline (Alfred Becht GmbH), Acroseal (Septodont), Adseal (META BIOMED), Perma Evolution (META BIOMED), EZ-Fill (Essentail Dental Systems).

The radiopacity of all samples was measured according to ISO 6876:2012.

The invention claimed is:
1. Dental composition comprising:
   (a) at least two di- or polyepoxides having 2 to 5 epoxide groups and having a molecular weight of from 200 to 700 Da, or a macromonomeric reaction product obtained by reacting the diepoxide with a dicarboxylic acid in a molar ratio [diepoxide]/[dicarboxylic acid] of at least 2;
   (b) one or more primary monoamines and/or disecondary diamines;
   (c) one or more aliphatic polyamines;
   (d) a particulate filler,
   wherein the molar ratio of epoxide groups in component (a) to the N—H bonds in component (b) and (c) [epoxide$_{(a)}$]/[N—H$_{(b),(c)}$] is in the range of from 0.9 to 1.1;
   wherein the at least two di- or polyepoxide having 2 to 5 epoxide groups is a compound of the following formula (I):

 (I)

wherein
   A represents an n-valent organic moiety having 1 to 10 heteroatoms selected from oxygen atoms and sulfur atoms; and
   B represents an m+1-valent organic moiety,
   Z is an epoxide group which may have a substituent, m which are independent from each other represent an integer of at least 1; and n is an integer of from 1 to 5;

wherein the m are selected so that 2 to 5 epoxide groups are present;

wherein the organic moiety in A of one of the di- or polyepoxides contains a phenylene moiety;

wherein the heteroatoms selected from oxygen atoms and sulfur atoms in A are present in ester bonds, ether bonds, thioether bonds or thioester bonds; and wherein the composition does not contain any of 2,2-bis-(4-hydroxyphenyl)-propane, 2,2-bis-(4-hydroxyphenyl)-methane, bisphenol-A diglycidyl ether or bisphenol-F diglycidyl ether.

2. The dental composition according to claim 1, wherein component (c) is present in an amount of from 5 to 95 percent by weight based on the total amount of (b) and (c) in the composition.

3. The dental composition according to claim 1, wherein component (c) is an aliphatic polyamine selected among compounds of the following structures:

[chemical structures]

wherein $R^{10}$ denotes hydrogen or a substituted or unsubstituted $C_1$ to $C_{18}$ alkyl group, a substituted or unsubstituted $C_3$ to $C_{18}$ cycloalkyl group, or a substituted or unsubstituted $C_7$ to $C_{18}$ aralkyl group, $R^{20}$ represents a difunctional substituted or unsubstituted $C_1$ to $C_{18}$ alkylene group, or a substituted or unsubstituted cycloalkylene group, A' denotes a moiety derived from a di- or polyepoxides that is capable of an addition reaction with an amine, and c is an integer.

4. A dental composition comprising:

(a) at least two di- or polyepoxides having 2 to 5 epoxide groups and having a molecular weight of from 200 to 700 Da, (b) one or more primary monoamines and/or disecondary diamines;

(c) one or more aliphatic polyamines;

(d) a particulate filler, wherein the molar ratio of epoxide groups in component (a) to the N—H bonds in component (b) and (c) [epoxide$_{(a)}$]/[N—H$_{(b),(c)}$] is in the range of from 0.9 to 1.1;

wherein the at least two di- or polyepoxide having 2 to 5 epoxide groups is a compound of the following formula (I):

$$A(BZ_m)_n \qquad (I)$$

wherein

A represents an n-valent organic moiety having 1 to 10 heteroatoms selected from oxygen atoms and sulfur atoms; and B represents an m+1-valent organic moiety, Z is an epoxide group which may have a substituent, m which are independent from each other represent an integer of at least 1; and n is an integer of from 1 to 5;

wherein the m are selected so that 2 to 5 epoxide groups are present;

wherein the organic moiety in A of one of the di- or polyepoxides contains a phenylene moiety;

wherein the heteroatoms selected from oxygen atoms and sulfur atoms in A are present in ester bonds, ether bonds, thioether bonds or thioester bonds;

wherein the at least two di- or polyepoxides having 2 to 5 epoxide groups are obtained by reacting one or more compounds having 2 to 5 hydroxyl groups with epichlorohydrin;

wherein one of the compound having 2 to 5 hydroxyl groups is resorcinol;

wherein BZ is a group of the formula (II) or (III):

[chemical structures (II) and (III)]

wherein

X is —NH—, an oxygen atom or a sulfur atom,

X' is —NH—, an oxygen atom or a sulfur atom,

X" is —NH—, an oxygen atom or a sulfur atom,

X'" is —CH$_2$—, —NH—, an oxygen atom or a sulfur atom, $R^{11}$ and $R^{12}$ which may be the same or different, independently represent a hydrogen atom or a straight chain or branched $C_{1-6}$ alkyl group, $R^{13}$ represents a hydrogen atom or a straight chain or branched $C_{1-6}$ alkyl group, $R^{14}$ represents a hydrogen atom, a hydroxyl group which may be substituted, or a straight chain or branched $C_{1-6}$ alkyl group, o represents an integer of from 2 to 10, p is an integer of from 0, 1 or 2;

q which may be the same or different, independently represent an integer of from 0 to 10;

v represents an integer of from 1 to 10;

and wherein the dental composition does not contain any of 2,2-bis-(4-hydroxyphenyl) propane, 2,2-bis-(4-hydroxyphenyl)-methane, bisphenol-A diglycidyl ether or bisphenol F diglycidyl ether.

5. The dental composition according to claim 1, wherein BZ is a group of the formula (II) or (III):

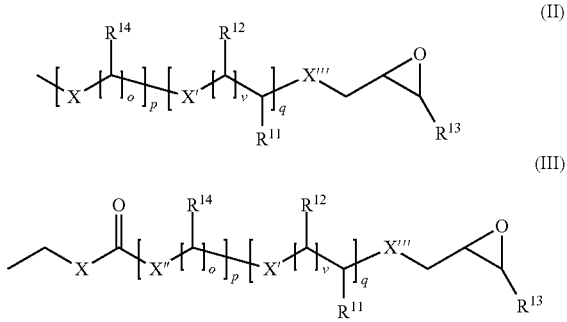

wherein
X is —NH—, an oxygen atom or a sulfur atom,
X' is —NH—, an oxygen atom or a sulfur atom,
X" is —NH—, an oxygen atom or a sulfur atom,
X''' is —CH$_2$—, —NH—, an oxygen atom or a sulfur atom,
R$^{11}$ and R$^{12}$
which may be the same or different, independently represent a hydrogen atom or a straight chain or branched C$_{1-6}$ alkyl group,
R$^{13}$ represents a hydrogen atom or a straight chain or branched C$_{1-6}$ alkyl group,
R$^{14}$
represents a hydrogen atom, a hydroxyl group which may be substituted, or a straight chain or branched C$_{1-6}$ alkyl group,
o represents an integer of from 2 to 10,
p is an integer of from 0, 1 or 2;
q which may be the same or different, independently represent an integer of from 0 to 10;
v represents an integer of from 1 to 10.

6. The dental composition according to claim 1, which is a root canal filling composition or a pulp capping composition.

7. The dental composition according to claim 1, wherein the composition is obtained by a process comprising a step of a step-growth polyaddition reaction of mixture containing at least two polymerizable di- or polyepoxides having 2 to 5 epoxide groups, or a macromonomeric reaction product obtained by reacting the diepoxide with a dicarboxylic acid in a molar ratio [diepoxide]/[dicarboxylic acid] of at least 2 with one or more primary monoamines and/or disecondary diamines and one or more aliphatic polyamines;
wherein the at least two di- or polyepoxide having 2 to 5 epoxide groups is a compound of the following formula (I):

wherein
A represents an n-valent organic moiety having 1 to 10 heteroatoms selected from oxygen atoms and sulfur atoms; and
B represents an m+1-valent organic moiety,
Z is an epoxide group which may have a substituent,
m which are independent from each other represent an integer of at least 1; and
n is an integer of from 1 to 5;
wherein the m are selected so that 2 to 5 epoxide groups are present;
wherein the molar ratio of epoxide groups in Formula 1 to the N—H bonds in primary monoamines and/or disecondary diamines and aliphatic amines [epoxide/NH] is in the range of from 0.9 to 1.1;
wherein the organic moiety in A of one of the di- or polyepoxides contains a phenylene moiety; and
wherein the heteroatoms selected from oxygen atoms and sulfur atoms in A are present in ester bonds, ether bonds, thioether bonds or thioester bonds;
and wherein the dental composition does not contain any of 2,2-bis-(4-hydroxyphenyl) propane, 2,2-bis-(4-hydroxyphenyl)-methane, bisphenol-A diglycidyl ether or bisphenol F diglycidyl ether.

8. The dental composition according to claim 4, wherein the composition is obtained by a process comprising a step of a step-growth polyaddition reaction of mixture containing at least two polymerizable di- or polyepoxides having 2 to 5 epoxide groups with one or more primary monoamines and/or disecondary diamines and one or more aliphatic polyamines;
wherein the at least two di- or polyepoxide having 2 to 5 epoxide groups is a compound of the following formula (I):

wherein
A represents an n-valent organic moiety having 1 to 10 heteroatoms selected from oxygen atoms and sulfur atoms; and
B represents an m+1-valent organic moiety,
Z is an epoxide group which may have a substituent,
m which are independent from each other represent an integer of at least 1; and
n is an integer of from 1 to 5;
wherein the m are selected so that 2 to 5 epoxide groups are present;
wherein the molar ratio of epoxide groups in Formula 1 to the N—H bonds in primary monoamines and/or disecondary diamines and aliphatic amines [epoxide/NH] is in the range of from 0.9 to 1.1;
wherein the organic moiety in A of one of the di- or polyepoxides contains a phenylene moiety;
wherein the heteroatoms selected from oxygen atoms and sulfur atoms in A are present in ester bonds, ether bonds, thioether bonds or thioester bonds;
wherein the at least two di- or polyepoxides having 2 to 5 epoxide groups is further obtained by reacting one or more compounds having 2 to 5 hydroxyl groups with epichlorohydrin; and
wherein one of the compound having 2 to 5 hydroxyl groups is resorcinol.

9. The dental composition according to claim 4, wherein component (c) is present in an amount of from 5 to 95 percent by weight based on the total amount of (b) and (c) in the composition.

10. The dental composition according to claim 4, wherein component (c) is an aliphatic polyamine selected among compounds of the following structures:

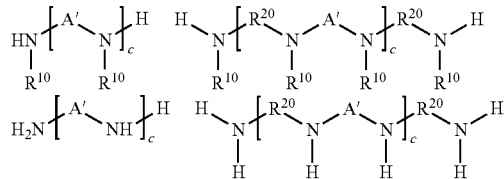

-continued

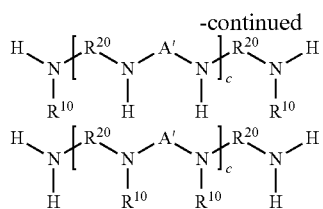

wherein $R^{10}$ denotes hydrogen or a substituted or unsubstituted $C_1$ to $C_{18}$ alkyl group, a substituted or unsubstituted $C_3$ to $C_{18}$ cycloalkyl group, or a substituted or unsubstituted $C_7$ to $C_{18}$ aralkyl group, $R^{20}$ represents a difunctional substituted or unsubstituted $C_1$ to $C_{18}$ alkylene group, or a substituted or unsubstituted cycloalkylene group, A' denotes a moiety derived from a di- or polyepoxides that is capable of an addition reaction with an amine, and c is an integer.

\* \* \* \* \*